United States Patent [19]
Coulie et al.

[11] Patent Number: 6,013,765
[45] Date of Patent: Jan. 11, 2000

[54] ISOLATED TUMOR REJECTION ANTIGENS DERIVED FROM DAGE TUMOR REJECTION ANTIGEN PRECUSOR

[75] Inventors: Pierre Coulie; Hideyuki Ikeda; Thierry Boon-Falleur, all of Brussels, Belgium

[73] Assignee: Ludwig Institute for Cancer Research, New York, N.Y.

[21] Appl. No.: 08/809,999

[22] PCT Filed: Sep. 21, 1995

[86] PCT No.: PCT/US95/12117

§ 371 Date: Apr. 9, 1997

§ 102(e) Date: Apr. 9, 1997

[87] PCT Pub. No.: WO96/10577

PCT Pub. Date: Apr. 11, 1996

Related U.S. Application Data

[63] Continuation-in-part of application No. 08/316,231, Sep. 30, 1994, Pat. No. 5,830,753.

[51] Int. Cl.[7] ........................................... C07K 7/06
[52] U.S. Cl. .............................. 530/328; 514/15; 514/16; 530/300; 530/828

[58] Field of Search ...................................... 530/300, 328, 530/828; 514/15, 16

[56] References Cited

U.S. PATENT DOCUMENTS 5,571,711  11/1996  Van Der Bruggen et al. .
5,587,289  12/1996  Lurquin et al. .
5,695,994  12/1997  Boo-Falleur et al. .

OTHER PUBLICATIONS

MPSRCH Protein Database searched Apr. 1998 Accession No. R76811, Mitsubishi et al, Jul. 1995.

*Primary Examiner*—Julie Reeves
*Attorney, Agent, or Firm*—Fulbright & Jaworski, LLP

[57] ABSTRACT

A new family of tumor rejection antigen precursors, and the nucleic acid molecules which code for them, are disclosed. These tumor rejection antigen precursors are referred to as DAGE tumor rejection antigen precursors, and the nucleic acid molecules which code for them are referred to as GAGE coding molecules. Various diagnostic and therapeutic uses of the coding sequences and the tumor rejection antigens, and their precursor molecules are described.

3 Claims, 5 Drawing Sheets

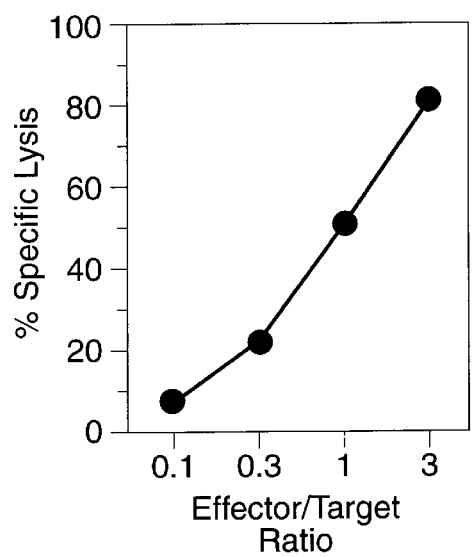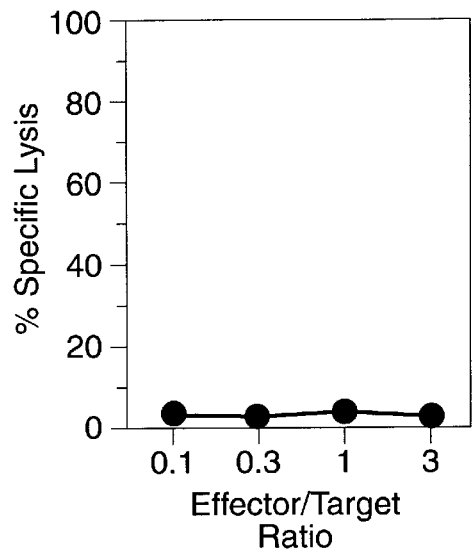
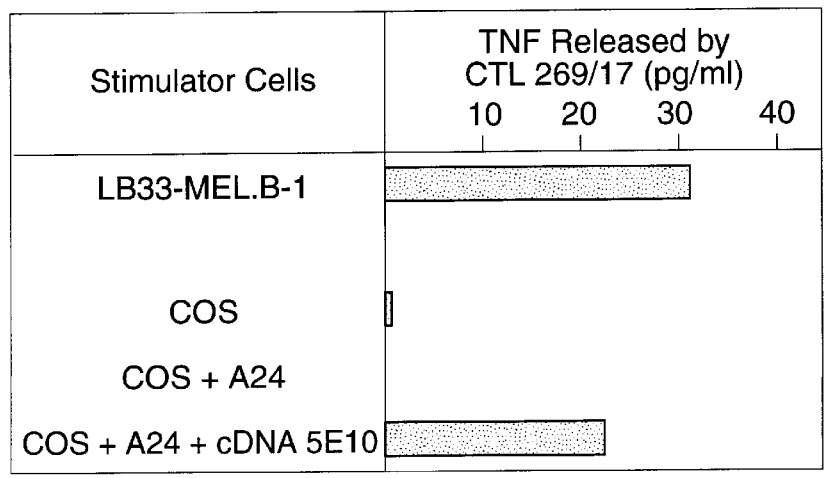

SEQUENCE LISTING (1) GENERAL INFORMATION:

(iii) NUMBER OF SEQUENCES:  18

(2) INFORMATION FOR SEQ ID NO: 1:

(i) SEQUENCE CHARACTERISTICS:
        (A) LENGTH:    1554 base pairs
        (B) TYPE:      nucleic acid
        (C) STRANDEDNESS:  double
        (D) TOPOLOGY:  linear (ii) MOLECULE TYPE: nucleic acid (ix) FEATURE:
        (A) NAME/KEY:  DAGE (5E10)

(xi) SEQUENCE DESCRIPTION: SEQ ID NO: 1:

```
GACTGAGACC TAGAAATCCA AGCGTTGGAG GTCCTGAGGC CAGCCTAAGT           50

TTCCGCAAAA TGGAACGAAG GCGTTTGCGG GGTTCCATTC AGAGCCGATA          100

CATCAGCATG AGTGTGTGGA CAAGCCCACG GAGACTTGTG GAGCTGGCAG          150
```

```
GGCAGAGCCT GCTGAAGGAT GAGGCCCTGG CCATTGCCGC CTGGAGTTG            200

CTGCCCAGGG AGCTCTTCCC GCCACTCTTC ATGGCAGCCT TTGACGGGAG           250

ACACAGCCAG ACCCTGAAGG CAATGGTGCA GGCCTGGCCC TTCACCTGCC           300

TCCCTCTGGG AGTGCTGATG AAGGGACAAC ATCTTCACCT GGAGACCTTC           350

AAAGCTGTGC TTGATGGACT TGATGTGCTC CTTGCCCAGG AGGTTCGCCC           400

CAGGAGGTGG AAACTTCAAG TGCTGGATTT ACGGAAGAAC TCTCATCAGG           450

ACTTCTGGAC TGTATGGTCT GGAAACAGGG CCAGTCTGTA CTCATTTCCA           500

GAGCCAGAAG CAGCTCAGCC CATGACAAAG AAGCGAAAAG TAGATGGTTT           550

GAGCACAGAG GCAGAGCAGC CCTTCATTCC AGTAGAGGTG CTCGTAGACC           600

TGTTCCTCAA GGAAGGTGCC TGTGATGAAT TGTTCTCCTA CCTCATTGAG           650

AAAGTGAAGC GAAAGAAAAA TGTACTACGG CTGTGCTGTA AGAAGCTGAA           700

GATTTTTGCA ATGCCCATGC AGGATATCAA GATGATCCTG AAAATGGTGC           750

AGCTGGACTC TATTGAAGAT TTGGAAGTGA CTTGTACCTG GAAGCTACCC           800

ACCTTGGCGA AATTTTCTCC TTACCTGGGC CAGATGATTA ATCTGCGTAG           850

ACTCCTCCTC TCCCACATCC ATGCATCTTC CTACATTTCC CCGGAGAAGG           900

AAGAGCAGTA TATCGCCCAG TTCACCTCTC AGTTCCTCAG TCTGCAGTGC           950

CTGCAGGCTC TCTATGTGGA CTCTTTATTT TTCCTTAGAG GCCGCCTGGA          1000

TCAGTTGCTC AGGCACGTGA TGAACCCCTT GGAAACCCTC TCAATAACTA          1050

ACTGCCGGCT TTCGGAAGGG GATGTGATGC ATCTGTCCCA GAGTCCCAGC          1100

GTCAGTCAGC TAAGTGTCCT GAGTCTAAGT GGGGTCATGC TGACCGATGT          1150

AAGTCCCGAG CCCCTCCAAG CTCTGCTGGA GAGAGCCTCT GCCACCCTCC          1200

AGGACCTGGT CTTTGATGAG TGTGGGATCA CGGATGATCA GCTCCTTGCC          1250

CTCCTGCCTT CCCTGAGCCA CTGCTCCCAG CTTACAACCT TAAGCTTCTA          1300

CGGGAATTCC ATCTCCATAT CTGCCTTGCA GAGTCTCCTG CAGCACCTCA          1350

TCGGGCTGAG CAATCTGACC CACGTGCTGT ATCCTGTCCC CCTGGAGAGT          1400

TATGAGGACA TCCATGGTAC CCTCCACCTG GAGAGGCTTG CCTATCTGCA          1450

TGCCAGGCTC AGGGAGTTGC TGTGTGAGTT GGGGCGGCCC AGCATGGTCT          1500

GGCTTAGTGC CAACCCCTGT CCTCACTGTG GGACAGAAC CTTCTATGAC           1550

CCGG                                                            1554

(2) INFORMATION FOR SEQ ID NO:2:

(i) SEQUENCE CHARACTERISTICS:
        (A) LENGTH:      2148 base pairs
        (B) TYPE:        nucleic acid
        (C) STRANDEDNESS: double
        (D) TOPOLOGY:    linear (ii) MOLECULE TYPE: nucleic acid (ix) FEATURE:
         (A) NAME/KEY:   DAGE (Hi2)

(xi) SEQUENCE DESCRIPTION: SEQ ID NO:2:

GCTTCAGGGT ACAGCTCCCC CGCAGCCAGA AGCCGGGCCT GCAGCCCCTC            50

AGCACCGCTC CGGGACACCC CACCCGCTTC CCAGGCGTGA CCTGTCAACA           100

GCAACTTCGC GGTGTGGTGA ACTCTCTGAG GAAAAACCAT TTTGATTATT           150
```

```
ACTCTCAGAC GTGCGTGGCA ACAAGTGACT GAGACCTAGA AATCCAAGCG      200

TTGGAGGTCC TGAGGCCAGC CTAAGTCGCT TCAAAATGGA ACGAAGGCGT      250

TTGTGGGGTT CCATTCAGAG CCGATACATC AGCATGAGTG TGTGGACAAG      300

CCCACGGAGA CTTGTGGAGC TGGCAGGGCA GAGCCTGCTG AAGGATGAGG      350

CCCTGGCCAT TGCCGCCCTG GAGTTGCTGC CCAGGGAGCT CTTCCCGCCA      400

CTCTTCATGG CAGCCTTTGA CGGGAGACAC AGCCAGACCC TGAAGGCAAT      450

GGTGCAGGCC TGGCCCTTCA CCTGCCTCCC TCTGGGAGTG CTGATGAAGG      500

GACAACATCT TCACCTGGAG ACCTTCAAAG CTGTGCTTGA TGGACTTGAT      550

GTGCTCCTTG CCCAGGAGGT TCGCCCCAGG AGGTGGAAAC TTCAAGTGCT      600

GGATTTACGG AAGAACTCTC ATCAGGACTT CTGGACTGTA TGGTCTGGAA      650

ACAGGGCCAG TCTGTACTCA TTTCCAGAGC CAGAAGCAGC TCAGCCCATG      700

ACAAAGAAGC GAAAAGTAGA TGGTTTGAGC ACAGAGGCAG AGCAGCCCTT      750

CATTCCAGTA GAGGTGCTCG TAGACCTGTT CCTCAAGGAA GGTGCCTGTG      800

ATGAATTGTT CTCCTACCTC ATTGAGAAAG TGAAGCGAAA GAAAAATGTA      850

CTACGCCTGT GCTGTAAGAA GCTGAAGATT TTTGCAATGC CCATGCAGGA      900

TATCAAGATG ATCCTGAAAA TGGTGCAGCT GGACTCTATT GAAGATTTGG      950

AAGTGACTTG TACCTGGAAG CTACCCACCT TGGCGAAATT TTCTCCTTAC      1000

CTGGGCCAGA TGATTAATCT GCGTAGACTC CTCCTCTCCC ACATCCATGC      1050

ATCTTCCTAC ATTTCCCCGG AGAAGGAAGA GCAGTATATC GCCCAGTTCA      1100

CCTCTCAGTT CCTCAGTCTG CAGTGCCTGC AGGCTCTCTA TGTGGACTCT      1150

TTATTTTTCC TTAGAGGCCG CCTGGATCAG TTGCTCAGGC ACGTGATGAA      1200

CCCCTTGGAA ACCCTCTCAA TAACTAACTG CCGGCTTTCG GAAGGGGATG      1250

TGATGCATCT GTCCCAGAGT CCCAGCGTCA GTCAGCTAAG TGTCCTGAGT      1300

CTAAGTGGGG TCATGCTGAC CGATGTAAGT CCCGAGCCCC TCCAAGCTCT      1350

GCTGGAGAGA GCCTCTGCCA CCCTCCAGGA CCTGGTCTTT GATGAGTGTG      1400

GGATCACGGA TGATCAGCTC CTTGCCCTCC TGCCTTCCCT GAGCCACTGC      1450

TCCCAGCTTA CAACCTTAAG CTTCTACGGG AATTCCATCT CCATATCTGC      1500

CTTGCAGAGT CTCCTGCAGC ACCTCATCGG GCTGAGCAAT CTGACCCACG      1550

TGCTGTATCC TGTCCCCCTG GAGAGTTATG AGGACATCCA TGGTACCCTC      1600

CACCTGGAGA GGCTTGCCTA TCTGCATGCC AGGCTCAGGG AGTTGCTGTG      1650

TGAGTTGGGG CGGCCCAGCA TGGTCTGGCT TAGTGCCAAC CCCTGTCCTC      1700

ACTGTGGGGA CAGAACCTTC TATGACCCGG AGCCCATCCT GTGCCCCTGT      1750

TTCATGCCTA ACTAGCTGGG TGCACATATC AAATGCTTCA TTCTGCATAC      1800

TTGGACACTA AAGCCAGGAT GTGCATGCAT CTTGAAGCAA CAAAGCAGCC      1850

ACAGTTTCAG ACAAATGTTC AGTGTGAGTG AGGAAAACAT GTTCAGTGAG      1900

GAAAAAACAT TCAGACAAAT GTTCAGTGAG GAAAAAAAGG GGAAGTTGGG      1950

GATAGGCAGA TGTTGACTTG AGGAGTTAAT GTGATCTTTG GGGAGATACA      2000

TCTTATAGAG TTAGAAATAG AATCTGAATT TCTAAAGGGA GATTCTGGCT      2050

TGGGAAGTAC ATGTAGGAGT TAATCCCTGT GTAGACTGTT GTAAAGAAAC      2100

TGTTGAAAAT AAAGAGAAGC AATGTGAAGC AAAAAAAAAA AAAAAAAA      2148
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:3:

GCCTGCTGAA GGATGAGGCC                                                20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:4:

GGTGCTGCAG GAGACTCTGC                                                20

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ii) MOLECULE TYPE: protein (ix) FEATURE:
        (A) NAME/KEY: DAGE peptide (xi) SEQUENCE DESCRIPTION: SEQ ID NO:5:

Leu Tyr Val Asp Ser Leu Phe Phe Leu
                5

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: DAGE peptide (xi) SEQUENCE DESCRIPTION: SEQ ID NO:6:

Ala Leu Tyr Val Asp Ser Leu Phe Phe Leu
                5                    10

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: protein (ix) FEATURE:
                 (A) NAME/KEY:  DAGE peptide (xi) SEQUENCE DESCRIPTION: SEQ ID NO:7:

Leu Tyr Val Asp Ser Leu Phe Phe
                 5

(2) INFORMATION FOR SEQ ID NO:8:

(i) SEQUENCE CHARACTERISTICS:
                 (A) LENGTH:    10 amino acids
                 (B) TYPE:      amino acid
                 (D) TOPOLOGY:  linear (ii) MOLECULE TYPE: protein (ix) FEATURE:
                 (A) NAME/KEY:  DAGE peptide (xi) SEQUENCE DESCRIPTION: SEQ ID NO:8:

Leu Tyr Val Asp Ser Leu Phe Phe Leu Arg
                 5                   10

(2) INFORMATION FOR SEQ ID NO:9:

(i) SEQUENCE CHARACTERISTICS:
                 (A) LENGTH:    10 amino acids
                 (B) TYPE:      amino acid
                 (D) TOPOLOGY:  linear (ii) MOLECULE TYPE: protein (ix) FEATURE:
                 (A) NAME/KEY:  HLA-A2 binding motif
                 (D) OTHER INFORMATION:   One of the Xaa's bet
                     be absent (xi) SEQUENCE DESCRIPTION: SEQ ID NO:9:

Xaa Leu Xaa Xaa Xaa Xaa Xaa Gly Xaa Leu
                 5                   10

(2) INFORMATION FOR SEQ ID NO:10:

(i) SEQUENCE CHARACTERISTICS:
                 (A) LENGTH:    9 amino acids
                 (B) TYPE:      amino acid
                 (D) TOPOLOGY:  linear (ii) MOLECULE TYPE: protein (ix) FEATURE:
                 (A) NAME/KEY:  HLA-A3 binding motif (xi) SEQUENCE DESCRIPTION: SEQ ID NO:10:

Xaa Leu Xaa Xaa Xaa Xaa Xaa Xaa Lys
                 5

(2) INFORMATION FOR SEQ ID NO:11:

(i) SEQUENCE CHARACTERISTICS:
                 (A) LENGTH:    9 amino acids
                 (B) TYPE:      amino acid
                 (D) TOPOLOGY:  linear (ii) MOLECULE TYPE: protein (ix) FEATURE:
                 (A) NAME/KEY:  HLA-A3 binding motif (xi) SEQUENCE DESCRIPTION: SEQ ID NO:11:

Xaa Leu Xaa Xaa Xaa Xaa Xaa Xaa Tyr
                5

(2) INFORMATION FOR SEQ ID NO:12:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (A) NAME/KEY:  HLA-A11 binding motif (xi) SEQUENCE DESCRIPTION: SEQ ID NO:12:

Xaa Xaa Xaa Xaa Xaa Xaa Xaa Lys Lys
                5

(2) INFORMATION FOR SEQ ID NO:13:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (A) NAME/KEY:  HLA-B7 binding motif (xi) SEQUENCE DESCRIPTION: SEQ ID NO:13:

Xaa Pro Arg Xaa Xaa Xaa Xaa Xaa Leu
                5

(2) INFORMATION FOR SEQ ID NO:14:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (A) NAME/KEY:  HLA-B8 binding motif (xi) SEQUENCE DESCRIPTION: SEQ ID NO:14:

Xaa Xaa Lys Xaa Lys Xaa Xaa Xaa Leu
                5

(2) INFORMATION FOR SEQ ID NO:15:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (A) NAME/KEY:  HLA-B44 binding motif (xi) SEQUENCE DESCRIPTION: SEQ ID NO:15:

Xaa Glu Xaa Xaa Xaa Asp Xaa Xaa Phe
                5

(2) INFORMATION FOR SEQ ID NO:16:

```
      (i) SEQUENCE CHARACTERISTICS:
          (A) LENGTH:    11 amino acids
          (B) TYPE:      amino acid
          (D) TOPOLOGY:  linear (ii) MOLECULE TYPE: protein (ix) FEATURE:
          (A) NAME/KEY:  HLA-A2 binding motif
          (D) OTHER INFORMATION:   One Xaa between the
              second Gly may be absent (xi) SEQUENCE DESCRIPTION: SEQ ID NO:16:

Xaa Leu Xaa Gly Xaa Xaa Xaa Xaa Gly Xaa Val
                 5                  10

(2) INFORMATION FOR SEQ ID NO:17:

(i) SEQUENCE CHARACTERISTICS:
          (A) LENGTH:    509 amino acids
          (B) TYPE:      amino acid
          (D) TOPOLOGY:  linear (ii) MOLECULE TYPE: protein (ix) FEATURE:
          (A) NAME/KEY:  DAGE amino acid sequence
              corresponding to SEQ ID NO:2

(xi) SEQUENCE DESCRIPTION: SEQ ID NO:17:
```

Met Glu Arg Arg Arg Leu Trp Gly Ser Ile Gln Ser Arg Tyr Ile Ser
                 5                  10                  15

Met Ser Val Trp Thr Ser Pro Arg Arg Leu Val Glu Leu Ala Gly Gln
             20                  25                  30

Ser Leu Leu Lys Asp Glu Ala Leu Ala Ile Ala Ala Leu Glu Leu Leu
         35                  40                  45

Pro Arg Glu Leu Phe Pro Pro Leu Phe Met Ala Ala Phe Asp Gly Arg
     50                  55                  60

His Ser Gln Thr Leu Lys Ala Met Val Gln Ala Trp Pro Phe Thr Cys
 65                  70                  75                  80

Leu Pro Leu Gly Val Leu Met Lys Gly Gln His Leu His Leu Glu Thr
                 85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

```
Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
            290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
                355                 360                 365

Leu Gln Ala Leu Leu Glu Arg Ala Ser Ala Thr Leu Gln Asp Leu Val
                370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

(2) INFORMATION FOR SEQ ID NO:18:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (A) NAME/KEY:  HLA-A27 binding motif (xi) SEQUENCE DESCRIPTION: SEQ ID NO:18:

Xaa Tyr Xaa Xaa Xaa Xaa Xaa Xaa Leu
```

ISOLATED TUMOR REJECTION ANTIGENS DERIVED FROM DAGE TUMOR REJECTION ANTIGEN PRECUSOR

RELATED APPLICATIONS

This application is the national stage 35 U.S.C. § 371 filing of PCT/US95/12117, filed Sep. 21, 1995, which is a continuation in part of application Ser. No. 08/316,231, filed Sep. 30, 1994 now U.S. Pat. No. 5,830,753, the disclosure of which is incorporated by reference.

FIELD OF THE INVENTION

This invention relates to a nucleic acid molecule which code for a tumor rejection antigen precursor. More particularly, the invention concerns genes, whose tumor rejection antigen precursor is processed, inter alia, into at least one tumor rejection antigen that is presented by HLA-A24 molecules. The tumor rejection antigen precursor, or "TRAP" may be processed into additional peptides presented by other MHC molecules, such as HLA-A1 and its alleles, HLA-A2, HLA-Cw*1601, HLA-B44, and so forth. The genes in question do not appear to be related to other known tumor rejection antigen precursor coding sequences, are expressed on a variety of tumors and, with the exception of testis, ovary and endometrial cells, are not expressed by normal cells.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774, incorporated by reference in its entirety. The "MAGE" family of tumor rejection antigen precursors is disclosed in this patent.

In U.S. patent application Ser. No. 938,334, now U.S. Pat. No. 5,405,940 the disclosure of which is incorporated by reference, it is explained that the MAGE-1 gene codes for a tumor rejection antigen precursor which is processed to nonapeptides which are presented by the HLA-A1 molecule. The nonapeptides which bind to HLA-A1 follow a "rule" for binding in that a motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); Rötzschke et al., Nature 348: 252–254 (1990); Bjorkman et al., Nature 329: 512–518 (1987); Traversari et al., J. Exp. Med. 176: 1453–1457 (1992). The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now U.S. Pat. No. 5,629,166 and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992 now abandoned, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993 now U.S. Pat. No. 5,571,711, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 and incorporated by reference herein, an unrelated tumor rejection antigen precursor, the so-called "BAGE" precursor is described. The BAGE precursor is not related to the MAGE family.

In U.S. patent applications Ser. No. 08/096,039 and Ser. No. 08/250,162, now U.S. Pat. Nos. 5,610,024 and 5,648,266, both of which are incorporated by reference, non-related TRAP precursor GAGE is also disclosed.

The work which is presented by the papers, patent, and patent applications cited supra deals, in large part, with the MAGE family of genes, and the unrelated BAGE and GAGE genes. It has now been found, however, that additional tumor rejection antigen precursors are expressed by cells. These tumor rejection antigen precursors are referred to as "DAGE" tumor rejection antigen precursors. They do not show homology to the MAGE family of genes, the BAGE gene, or the GAGE gene. Thus the present invention relates to genes encoding such TRAPs, the tumor rejection antigen precursors themselves as well as applications of both.

What further characterizes the DAGE tumor rejection antigen precursors is that their expression by tumor cells is much more widespread than the other tumor rejection antigen precursors described-previously. This is proven infra. Yet, the expression of the family by normal cells is again limited to testis, ovary and endometrial cells. Thus, a much more general means of assaying for the presence of transformed cells is available than previously. This will be seen by way of the examples.

The invention is elaborated upon further in the disclosure which follows.

BRIEF DESCRIPTION OF THE FIGURES

FIG. 1 describes, collectively, $^{51}$Cr release, cell lysis studies. In particular:

FIGS. 2A and 2B presents studies on the inhibition of lysis by cytolytic T cells in the presence of an anti-HLA-A24 monoclonal antibody. The studies were carried out in the presence or absence of 30 fold dilutions of culture medium of a hybridoma producing the HLA-A24 specific monoclonal antibody.

FIG. 3 shows the result of lysis experiments following transfection of LB804-ALL cells with the sequence Hi2.

DETAILED DESCRIPTION OF PREFERRED EMBODIMENTS

EXAMPLE 1

Melanoma cell line LB33-MEL.B was derived from a metastasis of patient LB33, using standard techniques. Tumor cells were then cloned by limiting dilution, resulting in clone LB33-MEL.B-1, used hereafter.

Samples containing mononuclear blood cells (which include lymphocytes) were taken from patient LB33. Samples of clone LB33-MEL.B-1 were contacted to the mononuclear blood cell samples. The mixtures were observed for lysis of the LB33-MEL.B-1 cells, this lysis indicating that cytolytic T cells ("CTLs") specific for a complex-of peptide and HLA molecule presented by the cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro. Prior to labelling, these cells were incubated for 48 hours, in the presence of 50 U/ml of IFN-γ to increase the expression of HLA Class I molecules. The cells were then resuspended at $10^7$ cells/ml in DMEM, supplemented with 10 mM HEPES and 30% FCS (i.e. fetal calf serum), and incubated for 45 minutes at 37° C. with 200 μCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. PBL containing samples were added in 100 ul of the same medium, and assays were carried out in duplicate. Plates were centrifuged for 4 minutes at 100 g, and incubated for four hours at 37° C. in a 5.5% CO$_2$ atmosphere.

Plates were centrifuged again, and 100 ul aliquots of supernatant were collected and counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100® to target cells.

Those mononuclear blood cell samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

Figure 1A:
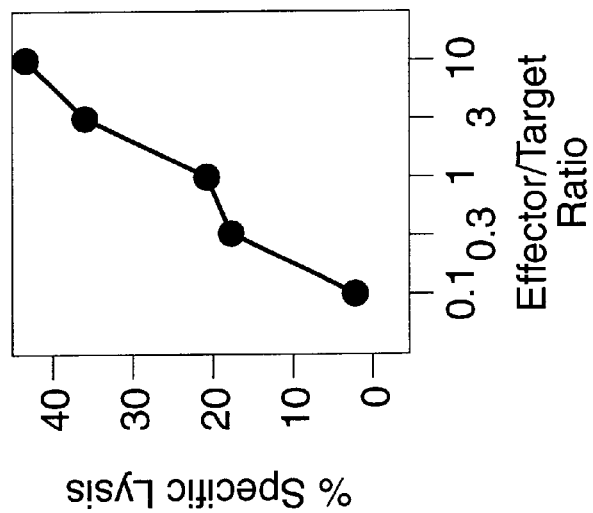
FIG. 1A shows lysis of cell line LB33-MEL.B-1.
Figure 1B:
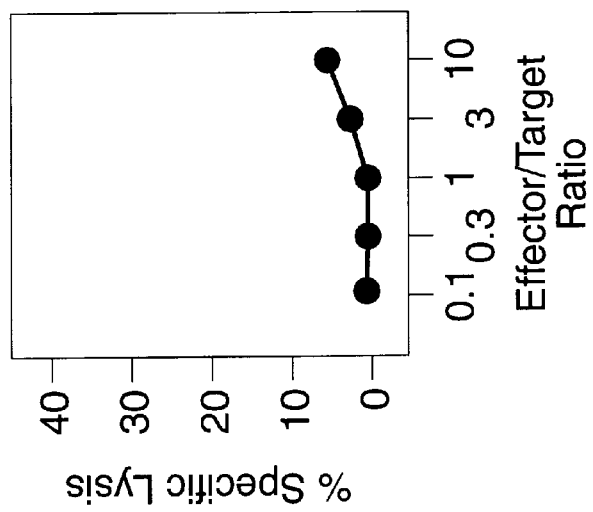
FIG. 1B shows lysis of LB33 B cells transformed by EBV. These are autologous cells.
Figure 1C:
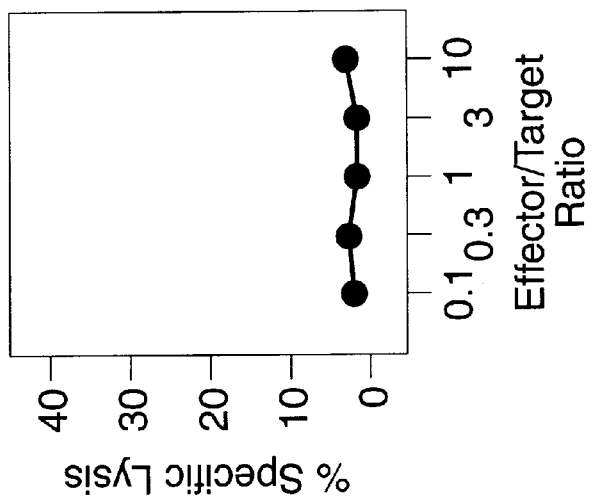
FIG. 1C shows lysis studies on NK target K562. In each case, the effector cells were CTL clone LB33-CTL-269/17.

These experiments led to isolation of CTL clone LB33-CTL-269/17 from patient LB33. As FIGS. 1A–1C indicate, this CTL clone lysed LB33-MEL.B-1 tumor cells, but not EBV transformed B cells of patient LB33, nor K562 cells. When the target cells were incubated with a monoclonal antibody specific to HLA-A24, lysis was inhibited, suggesting that any TRA peptide involved is presented by HLA-A24. FIGS. 2A and 2B show these results.

A second CTL clone, referred to as LB33-CTL-269/1, lysed LB33-MEL.B-1 but not EBV-B transformed B cells nor K562, thus suggesting that the same target antigen was recognized. Lysis by clone LB33-CTL-269/1 was also inhibited by the anti-HLA-A24 monoclonal antibody.

EXAMPLE 2

Having identified the presenting MHC, molecule as HLA-A24, studies were carried out to identify the coding sequence for the protein molecule, referred to hereafter as the "tumor rejection antigen precursor" or "TRAP" molecule which was the source of the presented peptide.

To do this, total RNA was isolated from cell line LB33-MEL.B-1. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into DH5α *E. coli* (electroporation conditions: 1 pulse at 25 μfarads, 2500 V).

The transfected bacteria were selected with ampicillin (50 μg/ml), and then divided into 400 pools of 100 clones each. Each pool represented about 50 different cDNAs, as analysis showed that all plasmids contained an insert and cloning was not directional. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

EXAMPLE 3

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, 100 ng of plasmid pcDNA-I/Amp-A2A and 100 ng of DNA of a pool of the cDNA library described supra. Plasmid pcDNA-I/Amp-A24 contains the HLA-A24 gene from LB33-MEL.B which was identified as allele HLA-A*2402. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of described CTL clone 269/1 were added, in 100 μl of Iscove's medium containing 10% pooled human serum. Supernatant was removed after 24 hours, and TNF content was determined in an assay on WEHI cells, as described by Traversari et al., Immunogenetics 35: 145–152 (1992), the disclosure of which is incorporated by reference.

Of 400 pools tested, one was positive.

EXAMPLE 4

The bacteria of the positive pool were subcloned. Plasmid DNA was extracted from 600 individual colonies, and cotransfected with pcDNA-I/Amp-A24 into new samples of COS cells in the same manner as described supra, and the cells were again tested for stimulation of CTL 269/1. A positive clone was found, identified as "5E10".

The plasmid from the positive clone was removed, and sequenced following art known techniques.

The sequence identified is 1554 base pairs long (see SEQ ID NO: 1). This sequence contains an open reading frame encoding 518 amino acids.

The 104 nucleotides at positions 1310–1413 were found to be identical to the 104 first base pairs of a 113 base pair sequence recorded in Genbank: L25344, HOMRBCESTC "Human (clone 17)" erythroleukemic expressed sequence tag (EST) mRNA fragment. No sequences were found which corresponded to the sequence of SEQ ID NO: 1, however.

EXAMPLE 5

Following the isolation of 5E10, described supra, it was used as a probe in a standard Northern Blot, using total RNA of LB 33-MEL, and standard techniques.

The results showed a band of about 2.5 kilobases, which is, of course, somewhat longer than the probe itself. This suggests that clone 5E10 is not complete. As a result, the same cDNA library prepared from RNA of LB33-MEL cells was screened, again using cDNA 5E10 as a probe. A cDNA clone of 2148 base pairs was identified, and sequenced. It is referred to as Hi2. The sequence of 5E10 is completely included in that of Hi2, except that at base 254, Hi2 has cytosine, while 5E10 has thymine.

EXAMPLE 6

Following the isolation of Hi2, a set of experiments were carried out in order to confirm that Hi2 was a tumor rejection antigen precursor encoding sequence. Specifically, HLA-A24 positive leukemia cell line LB804-ALL was used, because prior experiments had shown that CTL 269/17, described supra, did not lyse this line.

Cells of the leukemia line were transfected with expression vector pEF-BOS-puro.PL3, which carries a gene conferring puromycin resistance, and into which cDNA Hi2 was cloned. Puromycin resistant populations were selected, and isolated. These proved to be sensitive to CTL 269/17, thus indicating that expression of antigen LB33-E is not dependent upon the high copy number which results from COS-7 transfection.

FIG. 3 shows these results, where i.e., that the leukemia cell line before transfection, where CTL 269/17 is the responder.

The sequence of Hi2 is provided as SEQ ID NO:2. When comparing it to other sequences in data banks, it was found that nucleotides 1486–1589 are identical to 104 base pairs of a 113 base pair sequence expressed in myeloid leukemia cell line K562 (Gen Bank:L25344). Nucleotides 1983–2128 are identical to 146 of 147 base pairs expressed in promyelocytic leukemia cell line. HL-60 (DDBJ:D20455), while nucleotides 1736–2067 are 97% homologous with 325 base pairs of a 332 base pair cDNA found in cells of human testis (Gen Bank:T19428).

Analysis of the sequence of Hi2 shows an open reading frame encoding a putative protein of 509 amino acids, which has no signal sequence. No significant homology was found with other protein sequences in data banks.

EXAMPLE 7

Hi2 was then used to isolate genomic DNA encoding the pertinent protein. The DNA of 12 groups of 70,000 cosmids of a human genomic DNA library was collected, and 5E10 was used to hybridize to these, using standard methodologies. The clone hybridized to one cosmid group. Following subcloning one cosmid was identified which hydridized with cDNA clone 5E10. The sequence was secured by using primers deduced from the cDNA sequence. The sequence presents six exons, with the open reading frame spanning exons 3–6.

EXAMPLE 8

The information in SEQ ID NO: 1 was sufficient to permit analysis of gene expression via polymerase chain reaction (PCR).

The following primers were used:
5'-GCCTGCTGAAGGATGAGGCC-3' (SEQ ID NO: 3)
5'-GGTGCTGCAGGAGACTCTGC-3' (SEQ ID NO: 4)
These correspond to nucleotides 157–176, and the reverse complement of nucleotides 1328–1347 of SEQ ID NO: 1, respectively. NO: 1, respectively.
The PCR was carried out for 28 cycles, (1 cycle: 1 minute 94° C., 2 minutes at 65° C., 3 minutes at 72° C.). In carrying out the PCR, 2.5 ul of cDNA template, prepared as described supra, was combined with 2.5 ul of 10x Dynazyme buffer, 0.25 ul of each dNTP (10 mM), 0.5 ul of each primer (20 mM), 0.5U Dynazyme (0.25 ul stock, 2 U/ml), and 18.5 ul water. Table 1, which follows, sets forth the results. Note the expression over a number of varied tumor samples, as well as tumor cell lines, indicating that this is not an artifact of cell culture. Further, with the exception of testis, there is absolutely no expression in normal tissues.

TABLE 1

Expression of the gene corresponding to cDNA clone 5E10 in tumors and normal tissues

| Normal tissues: | |
| --- | --- |
| Liver | 0/1 |
| Stomach | 0/1 |
| Colon | 0/1 |
| Lung | 0/1 |
| Spleen | 0/1 |
| Heart | 0/1 |
| Breast | 0/1 |
| Bladder | 0/1 |
| Prostate | 0/1 |
| Thymus | 0/1 |
| Bone marrow | 0/1 |
| Blood lymphocytes | 0/1 |
| Fibroblasts | 0/1 |
| Testis | 2/2 |
| Tumor samples: | |
| Melanoma | 5/5 |
| Lymphoma | 2/5 |
| Chronic Myeloid Leukemia | 1/2 |
| Chronic Lymphoid Leukemia | 1/5 |
| Acute Myeloid Leukemia | 0/6 |
| Renal Carcinoma | 3/6 |
| Sarcoma | 2/3 |
| Breast carcinoma | 2/5 |
| Tumor cell lines: | |
| Melanoma | 11/15 |
| Leukemia | 3/6 |
| Burkitt lymphoma | 2/4 |

EXAMPLE 9

A second assay was carried out, based upon TNF (tumor necrosis factor) release. In this assay, COS-7 cells (10,000 cells/mirowell) were transfected with the plasmid pcDNAI/Amp carrying HLA-A24 cDNA, as described supra, or cotransfected with this plasmid and plasmid pcDNAI/Amp containing SEQ ID. NO: 1, described supra. Twenty four hours after transfection, 3000 cells of CTL 269/17 were added to the transfectants. In a control, the same number of LB33-MEL.B-1 cells were used. The concentration of TNF released in the cell medium was measured after 24 hours, using TNF sensitive cell line WEHI-164c13.

Figure 4A:
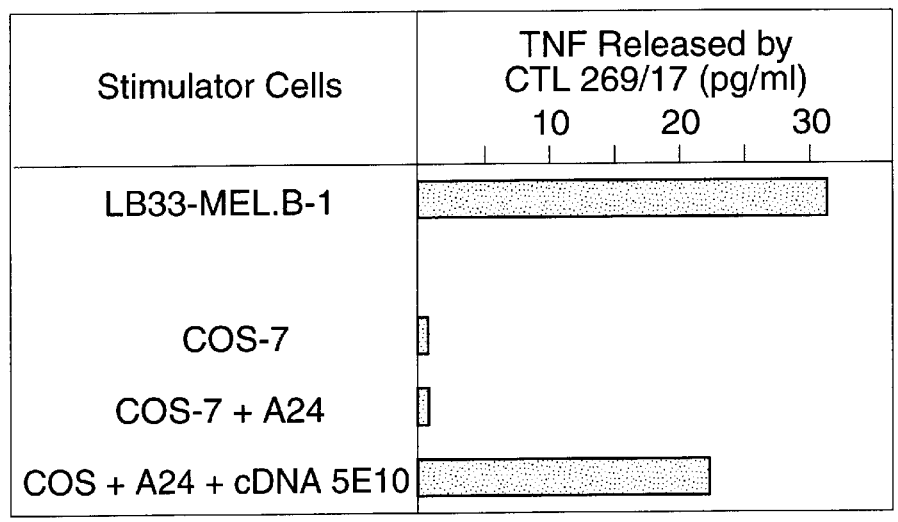
FIGS. 4A, 4B and 4C show the results obtained in a TNF release assay using CTL 269/17. The stimulator cells were either LB33-MEL.B-1, COS-7 cells, COS-7 cells transfected with a cDNA sequence coding for HLA-A24, or COS-7 cells transfected with both cDNA sequence coding for HLA-A24, and cDNA coding for a tumor rejection antigen precursor in accordance with this invention.
Figure 4B:
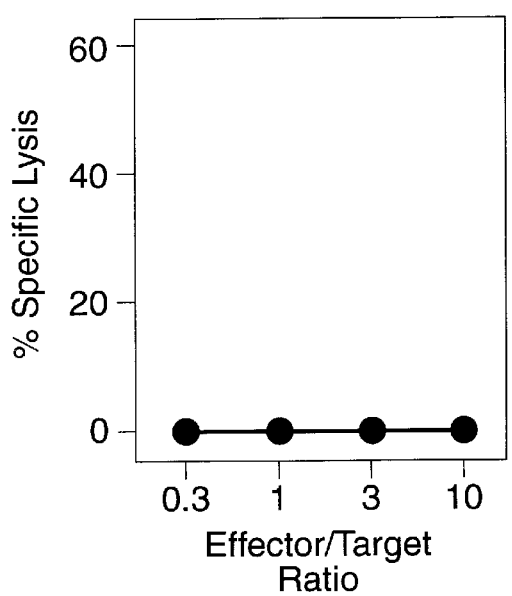
Figure 4C:
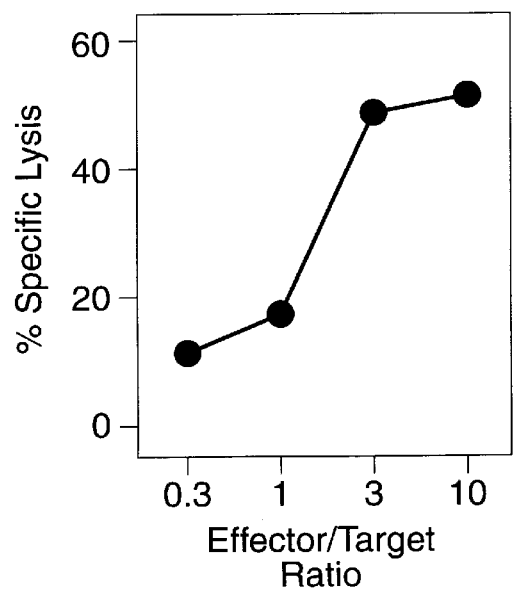

The results are presented in FIGS. 4A, 4B and 4C. They show that TNF release by CTLs was provoked only with COS cells cotransfected with vectors expressing HLA-A24 and SEQ ID NO 1. COS cells do not present HlA-A24 on their own, nor do they express the sequences of the invention. When cotransfected, however, they were able to provoke TNF release to a level nearly that of autologous cell line LB33-MEl.B-1.

The results, as set forth in FIG. 3, not only show that the material of SEQ ID NO: 1 does in fact code for a tumor rejection antigen precursor which stimulates CTLs when processed, it also shows that, as elaborated upon infra, one can assay for the presence of CTLs which are specific for tumor cells by using non-transformed cells, such that the resulting transfectant will express both HLA-A24 and DAGE.

EXAMPLE 10

As it has been well established that TRAPs are processed to smaller tumor rejection antigens, experiments were undertaken to identify a tumor rejection antigen or antigens produced from the described sequences.

The cDNA for 5E10 was partially digested with the endonuclease NsiI, and the thus truncated cDNA clones were cotransfected into COS-7 cells with HLA-A24 cDNA clones. Transfectants were then tested for expression of LB33-E, by adding CTL 269/17, and measuring TNF production.

Figure 5:
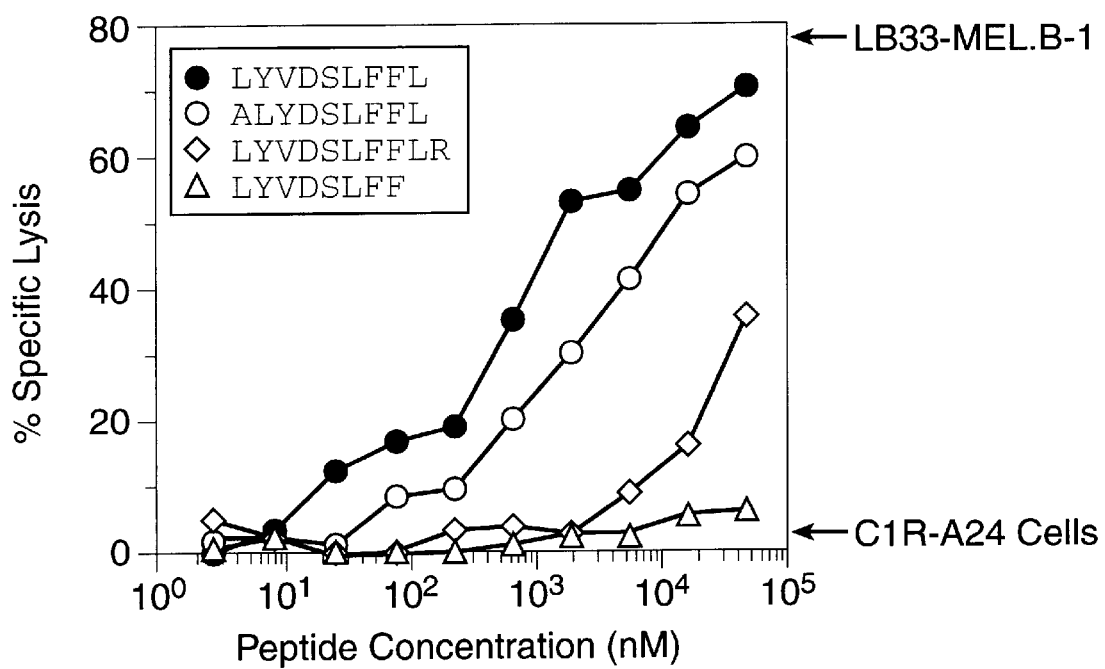
FIG. 5 compares induced lysis using various peptides derived from DAGE.

Results are summarized in FIG. 5. Nucleotides corresponding to nucleotides 1047–1260 of the cDNA of Hi2 were found to encode the relevant antigen. Four sequences in this region which (i) were 9 or 10 amino acids long, (ii) had Tyr or Phe at position 2, and (iii) had one of Phe, Leu, Ile, or Trp at C-terminus were possible. This is the motif for HLA-A24 binding described by Kubo, et al, J. Immunol 152:3913 (1994); Meier, et al, Immunogenetics 40:306–308 (1994). These were synthesized, and incubated with cells of MHC class I negative B-cell lymphoblastoid line C1R, which had been transfected with the HLA-A24 cDNA clone described supra. One peptide:

Leu Tyr Val Asp Ser Leu Phe Phe Leu (SEQ ID NO. 5), was found to sensitize the transfected C1R-A24 cells to lysis by the anti LB33-E CTLs, with half maximal effect at 500 nM.

Figure 6:
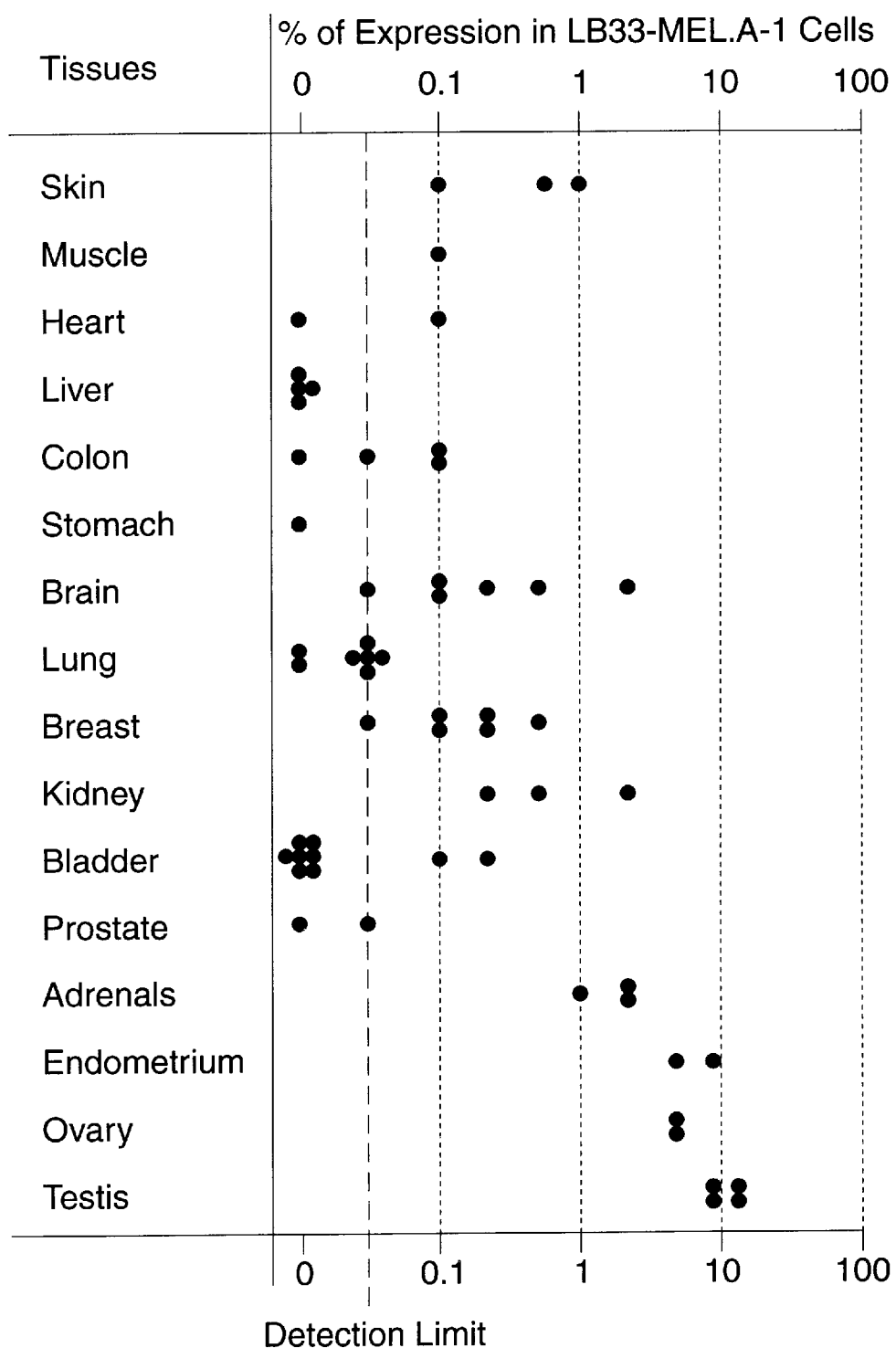
FIG. 6 shows the expression of DAGE in various tissue samples.

Comparative experiments were carried out, wherein peptides containing one additional N- or C-terminal amino acid, and where the C-terminal Leu was deleted, were used. SEQ ID NO:6 sensitized the cells to lysis, although to a lesser degree than SEQ ID NO:5. SEQ ID NOS : 7 and 8 were much less sensitive in sensitizing the cells, as is shown in FIG. 6. Peptides used extended SEQ ID NO:5 at the N-terminus with Ala (SEQ ID NO:6), and by deleting the C-terminal Leu (SEQ ID NO:7). Addition of Arg to the C terminus resulted in SEQ ID NO:8. In these experiments, $^{51}$Cr labeled C1R-A24 cells were incubated for 30 minutes in the presence of indicated peptide concentrations CTLs were added at E/T ratios of 10:1, and chromium release was measured after 4 hours.

EXAMPLE 11

Tests were then carried out, using the well known reverse transcriptase polymerase chain reaction ("RT-PCR"), to determine expression of the subject gene. In table 2, which follows the results are shown.

The higher proportion of positive tumors were melanomas (91%), lung squamous carcinomas (78%), and adenocarcinomas (46%), as well as renal carcinomas (43%), sarcomas (40%), and acute leukemias (33%).

There was also some expression in normal tissues. Testis, ovary, and endometrium expressed about 10% of what was found in cell line LB33-MEL, while lower levels were found in skin, brain, heart, kidney, and adrenal tissue. Note Table 2 and FIG. 6.

TABLE 2

Expression of gene DAGE by tumoral tissues.

| Tumor samples | | |
| --- | --- | --- |
| Brain tumors | 1/7 | |
| Colorectal carcinomas | 2/51 | 4% |

TABLE 2-continued

Expression of gene DAGE by tumoral tissues.

| | | |
|---|---|---|
| Gastric carcinomas | 1/2 | |
| Naevi | 9/18 | |
| Melanomas | | |
| primary legions | 43/49 | 88% |
| metastases | 144/152 | 95% |
| ocular | 5/9 | |
| Neuroblastomas | 2/3 | |
| Head and neck squamous carcinomas | 17/44 | 39% |
| Lung carcinomas | | |
| SCLC | 1/4 | |
| NSCLC | | |
| adenocarcinomas | 12/26 | 46% |
| squamous carcinomas | 51/65 | 78% |
| Prostatic carcinomas | 2/20 | |
| Renal carcinomas | 24/56 | 43% |
| Bladder tumors | | |
| superficial | 4/36 | 11% |
| infiltrating | 9/42 | 21% |
| Sarcomas | 10/25 | 40% |
| Mammary carcinomas | 45/169 | 27% |
| Thyroid carcinomas | 3/5 | |
| Acute leukemias | 21/63 | 33% |
| Tumor cell lines | | |
| Melanomas | 72/74 | 97% |
| Sarcomas | 4/5 | |
| Lung carcinomas | | |
| SCLC | 19/27 | 70% |
| NSCLC | 2/2 | |
| Mesotheliomas | 2/18 | |
| Head and neck tumors | 2/7 | |
| Bladder tumors | 2/3 | |
| Colorectal carcinomas | 1/15 | |
| Renal carcinomas | 9/12 | |
| EBV-transformed lymphoblastoid B cell lines | 0/8 | |

The foregoing examples show the isolation of a nucleic acid molecule which codes for a tumor rejection antigen precursor. This "TRAP" coding molecule, however, is not homologous with any of the previously disclosed MAGE, BAGE or GAGE coding sequences described in the references set forth supra. Hence, one aspect of the invention is an isolated nucleic acid molecule having the nucleotide sequence set forth in SEQ ID NO: 1 or SEQ ID NO: 2, as well as those portions of SEQ ID NO: 1 or SEQ ID NO:2 which express TRAs such as those encoding SEQ ID NOS : 5, 6 and 8 presented by MHC molecules such as HLA-A24, and derived from DAGE. This sequence is not a MAGE, BAGE or GAGE coding sequence, as will be seen by comparing it to the sequence of any of these genes as described in the cited references. Also a part of the invention are those nucleic acid sequences which also code for a non-MAGE, non-BAGE and non-MAGE tumor rejection antigen precursor but which hybridize to the nucleic acid molecule having the nucleotide sequence of SEQ ID NO: 1 and/or 2 under stringent conditions. The term "stringent conditions" as used herein refers to parameters with which the art is familiar. More specifically, stringent conditions, as used herein, refers to hybridization in 1M NaCl, 1% SDS, and 10% dextran sulfate. This is followed by two washes of the filter at room temperature for 5 minutes, in 2×SSC, and one wash for 30 minutes in 2×SSC, 0.1% SDS. There are other conditions, reagents, and so forth which can be used, which result in the same or higher degree of stringency. The skilled artisan will be familiar with such conditions, and, thus, they are not given here.

The widespread distribution in the expression of this gene (7 out of 8 types of tumor were found to express it), shows that the isolated nucleic acid molecule can be used as a diagnostic probe to determine presence of transformed cells. The identification of melanoma was 100%, so on a very basic level, the isolated nucleic acid molecules may be used to determine whether or not melanoma is present. Note that there are many ways available to the skilled artisan to confirm that a tumor sample is a melanoma sample, and these need not be reiterated here. Further, the rate of success in identifying tumors is in accordance with nucleic acid based diagnostic methods for determining transformation of cells.

It will also be seen from the examples that the invention embraces the use of the sequences in expression vectors, which may be used to transform or to transfect host cells and cell lines, be these prokaryotic (e.g., *E. coli*), or eukaryotic (e.g., CHO or COS cells). The expression vectors require that the pertinent sequence, i.e., those described supra, be operably linked to a promoter. As it has been found that human leukocyte antigen HLA-A24 presents a tumor rejection antigen derived from these genes, the expression vector may also include a nucleic acid sequence coding for HLA-A24. In a situation where the vector contains both coding sequences, it can be used to transform or transfect a cell which does not normally express either one. The tumor rejection antigen precursor coding sequence may be used alone, when, e.g., the host cell already expresses HLA-A24. Of course, there is no limit on the particular host cell which can be used. As the vectors which contain the two coding sequences may be used in HLA-A24 presenting cells if desired, and the gene for tumor rejection antigen precursor can be used in host cells which do not express HLA-A24.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE, BAGE and GAGE materials, the invention shall be referred to as the DAGE family of genes and TRAPs. Hence, whenever "DAGE" is used herein, it refers to the tumor rejection antigen precursors coded for by the previously described sequences. "DAGE coding molecule" and similar terms, are used to describe the nucleic acid molecules themselves.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-A24. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF or $^{51}$Cr release assay, of the types described supra.

The isolation of the TRAP gene also makes it possible to isolate the TRAP molecule itself, especially TRAP molecules containing the amino acid sequence coded for by SEQ ID NO: 2. These isolated molecules when presented as the TRA, or as complexes of TRA and HLA, such as HLA-A24, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provide a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular. Melanoma is well known as a cancer of pigment producing cells.

Therapeutic approaches based upon the disclosure are premised on a response by a subject's immune system, leading to lysis of TRA presenting cells, such as HLA-A24 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257: 238 (7-10-92); Lynch et al., Eur. J. Immunol. 21: 1403–1410 (1991); Kast et al., Cell 59: 603–614 (11-17-89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a DAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a GAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. U.S.A. 88: 110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A24 presenting cells which then present the HLA/peptide complex of interest. The TRAP is processed to yield the peptide partner of the HLA molecule while the TRA is presented without the need for further processing.

Also a feature of this invention are isolated peptides derived from the DAGE TRAP which conform to the rules for presentation by MHC molecules. For example, in PCT application No. PCT/US93/07421, incorporated by reference herein, several motifs are described as being associated with different MHC molecules. These motifs, incorporated by reference herein, as well as those taught by, e.g. Falk et al., Nature 351: 290–296 (1991); Engelhard, Ann. Rev. Immunol 12: 181–207 (1994); Ruppert et al., Cell 74: 929–937 (1993); Rötzschke et al., Nature 348: 252–254 (1990); Bjorkman et al., Nature 329: 512–518 (1987) and Traversari et al., J. Exp. Med. 176: 1453–1457 (1992) all of which are incorporated by reference, serve as a basis for identifying appropriate peptides obtainable or derivable from the DAGE gene. These peptides may be used alone, or in mixtures, in another aspect of the invention, which is now described. Exemplary of these are the following. For HLA-A2, a binding motif is Xaa Leu Xaa Gly $(Xaa)_n$ Leu (SEQ ID NO: 9) where n is 4 or 5. Amino acids 100–108 of SEQ ID NO: 17 correspond to this motif. A second motif for HLA-A2 replaces terminal Leu with Val (SEQ ID NO: 16), and amino acids 355–374 364 of SEQ ID NO: 17 satisfy this motif. For HLA-A3, the motifs are Xaa Leu $(Xaa)_6$ (Lys or Tyr) (SEQ ID NO: 10 and SEQ ID NO: 11). Amino acids 28–36, 80–88, 118–126, of SEQ ID NO: 17 well satisfy this motif. For HLA-A11, the motif $(Xaa)_7$ Lys Lys (SEQ ID No: 17) is known, and amino acids 150–158, 195–203, and 204–212 will satisfy it. For HLA-A24, the known motif is Xaa Tyr $(Xaa)_6$ Leu, (SEQ ID NO: 18) and is satisfied by amino acids 254–262, and 447–455 as well as SEQ ID NO: 5. For HLA-B7, the motif is Xaa Pro Arg $(Xaa)_5$ Leu, (SEQ ID NO: 14) and amino acids 48–56 meet it. For HLA-B8, $(Xaa)_2$ Lys Xaa Lys $(Xaa)_3$ Leu (SEQ ID No: 14) is the motif, satisfied by amino acids 156–164 and 198–206. For HLA-B44, motif Xaa Glu $(Xaa)_3$ Asp $(Xaa)_2$Phe (SEQ ID NO: 15) is satisfied by amino acids 184–192. For HLA-Cw*1601 the motif Xaa Alas $(Xaa)_6$ Leu here is satisfied by amino acids 40–48, and 375–383 of SEQ ID NO: 17.

The fact that a number of sequences are present which correspond to HLA motifs suggests what will be referred to herein as "cocktail" therapeutic and diagnostic uses. It is expected that in a typical CTL response to tumor cells, CTLs specific to more than one complex of peptide and HLA molecule will proliferate. For example, it may be the case that for HLA-A24 presenting cells, CTLs specific for HLA-A24 and amino acid sequence 467–475 will proliferate.

Thus, one can optimize the assay by using both peptides when attempting to identify CTLs. Similarly, the therapeutic methods might be optimized by using more than one HLA-A24 binding peptide.

It is well known that individuals are not "monovalent" for HLA molecules, as cells present more than one kind of HLA. Thus, one can maximize diagnostic and/or therapeutic by combining a number of peptides as described supra in a diagnostic assay to determine CTLS, or to treat patients in the therapies described supra.

Any concern as to false positives, is believed to be misplaced because, as noted supra, the nucleic acid molecules of the invention have been found to be expressed only in tumor cells, so the presence of CTLs to the HLA and the peptides must be considered de facto evidence of the presence, at some time in the past of the present existence of a cancerous or transformed condition. Thus, cocktails of the peptides of the invention can be prepared. Determination of the components of the mixture is not difficult, because all that is needed is one or more of the HLA types presented by the individual under consideration. HLA typing is a very standard technique, well known in the art; and well within the abilities and skill of the artisan.

It has been fairly well established that the blood of individuals afflicted with tumors frequently contains cytolytic T cells ("CTLs") against complexes of MHC molecules and presented peptides. See, e.g., Robbins et al., Canc. Res. 54: 3124–3126 (1994); Topolian et al., J. Immunol. 142: 3714–3725 (1989); Coulie et al., Int. J. Cancer 50: 289–297 (1992), all of which are incorporated by reference. Also, note Kawakami et al., J. Exp. Med. 180: 347–352 (1994); Hom et al., J. Immunother 10: 153–164 (1991), Darrow et al, J. Immunol. 142(9): 3329–3335 (1989); Slovin et al., J. Immunol. 137(9): 3042–3048 (1986), all of which are incorporated by reference. These papers all establish the usefulness of a CTL proliferation assay to diagnose cancer. Expressed generally, one takes a peripheral blood lymphocyte (PBL) containing sample from a subject to be tested. Assuming that the patient does have a tumor, or the subject's cells have began to undergo transformation, CTLs which are specific to transformed cells with be contained in that sample. These CTLs can be stimulated to proliferate via contact with a target cell which presents complexes of a relevant MHC molecule and the peptide presented thereby. For example, as was shown, supra, DAGE derived tumor rejection antigens ("TRAs") are presented by HLA-A24 cells. Thus, by mixing the PBL sample with a target of HLA-A24 presenting cells and peptides which are derived from a TRAP and presented by HLA-A24, one can observe CTL proliferation, and thus diagnose for the presence of transformed cells. These cells can be cells which normally present the MHC molecule in question, but can also be cells transformed by an HLA coding sequence. The cells may be tumor cells, or normal cells. Various ways of determining CTL proliferation are known, including TNF release assays, and $^{51}$Cr release assays. Other methodologies are also available. Thus, one aspect of the invention involves mixing a target cell sample with a peptide or mix of peptides derived from a DAGE TRA and presented by the MHC molecules of the target cell sample and with the PBLs of the subject under evaluation. The mixture is then tested for CTL proliferation.

The peptide or peptides may also be combined with one or more adjuvants which stimulate a more pronounced CTL response. Exemplary of such adjuvants are saponins and their derivatives, such as those disclosed by U.S. Pat. No. 5,057,540 to Kensil et al., incorporated by reference or PCT application PCT/US92/03579 to Scott et al., also incorporated by reference. Of course, standard adjuvants, such as Freund's complete adjuvant, or Freund's incomplete adjuvant, may also be used.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated peptide selected from the group consisting of (i) the peptide whose amino acid sequence consists of SEQ ID NO: 5, and (ii) the peptide where amino acid sequence consists of SEQ ID NO: 6.

2. The isolated peptide of claim 1, whose amino acid sequence consists of SEQ ID NO: 6.

3. The isolated peptide of claim 1, whose amino acid sequence consists of SEQ ID NO: 5.

* * * * *

UNITED STATES PATENT AND TRADEMARK OFFICE
CERTIFICATE OF CORRECTION

PATENT NO. : 6,013,765
DATED : January 11, 2000
INVENTOR(S) : Coulie, et al.

It is certified that error appears in the above-identified patent and that said Letters Patent is hereby corrected as shown below:

On the cover page, in the section entitled References Cited, U.S. Patent Documents, change "Boo-Falleur" to -- Boon-Falleur --.
In column 2, line 55, after "1993" add -- now U.S. Patent No. 5, 571, 711 --.
In column 3, line 11, delete the dash between the words "described" and "previously".
In column 6, line 23, change "i.e., that" to -- where 3A shows --.
In column 6, line 63, delete -- No:1, respectively -- because it has been repeated twice.
In column 12, line 43, delete "374"
In column 12, line 48, change "17" to -- 12 --.
In column 12, line 58, change "Alas (Xaa)$_6$ Leu here" to -- Ala (Xaa)$_6$ here --.
In column 12, line 58, before "is" add -- binding --.

Signed and Sealed this

Eighth Day of May, 2001

*Attest:*

NICHOLAS P. GODICI

*Attesting Officer*   Acting Director of the United States Patent and Trademark Office